United States Patent [19]

Santilli et al.

[11] 3,940,395
[45] Feb. 24, 1976

[54] 4-AMINO-2-PHENYL-6-THIOPRYIMIDINES

[75] Inventors: Arthur A. Santilli, Havertown; Dong H. Kim, Wayne, both of Pa.

[73] Assignee: American Home Products Corporation, New York, N.Y.

[22] Filed: Apr. 23, 1971

[21] Appl. No.: 137,060

Related U.S. Application Data

[60] Continuation-in-part of Ser. No. 854,300, Aug. 29, 1969, abandoned, Division of Ser. No. 590,198, Oct. 28, 1966, Pat. No. 3,498,984.

[52] U.S. Cl. ..................... 260/256.5 R; 260/251 R; 260/256.4 N; 424/251
[51] Int. Cl.² ...................................... C07D 239/40
[58] Field of Search ................... 260/256.5, 256.5 R

[56] References Cited
UNITED STATES PATENTS 3,498,984  3/1970  Santilli et al. ............... 260/256.5 R

*Primary Examiner*—R. Gallagher
*Attorney, Agent, or Firm*—Joseph Martin Weigman

[57] ABSTRACT

The invention is directed to 4-amino-2-phenyl-6-thiopyrimidine compounds having the formula

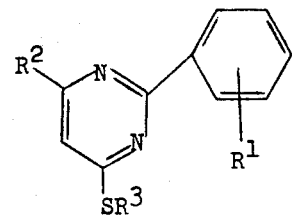

where $R^1$-$R^3$ are as defined in the specification. The compounds have pharmacodynamic activity as central nervous system depressants. That is, they produce a calming effect in the host.

20 Claims, No Drawings

4-AMINO-2-PHENYL-6-THIOPRYIMIDINES

This application is a continuation-in-part of our application Ser. No. 854,300 filed Aug. 29, 1969 now abandoned which was in turn a division of our application Ser. No. 590,198 filed Oct. 28, 1966 now U.S. Pat. No. 3,498,948 issued Mar. 3, 1970.

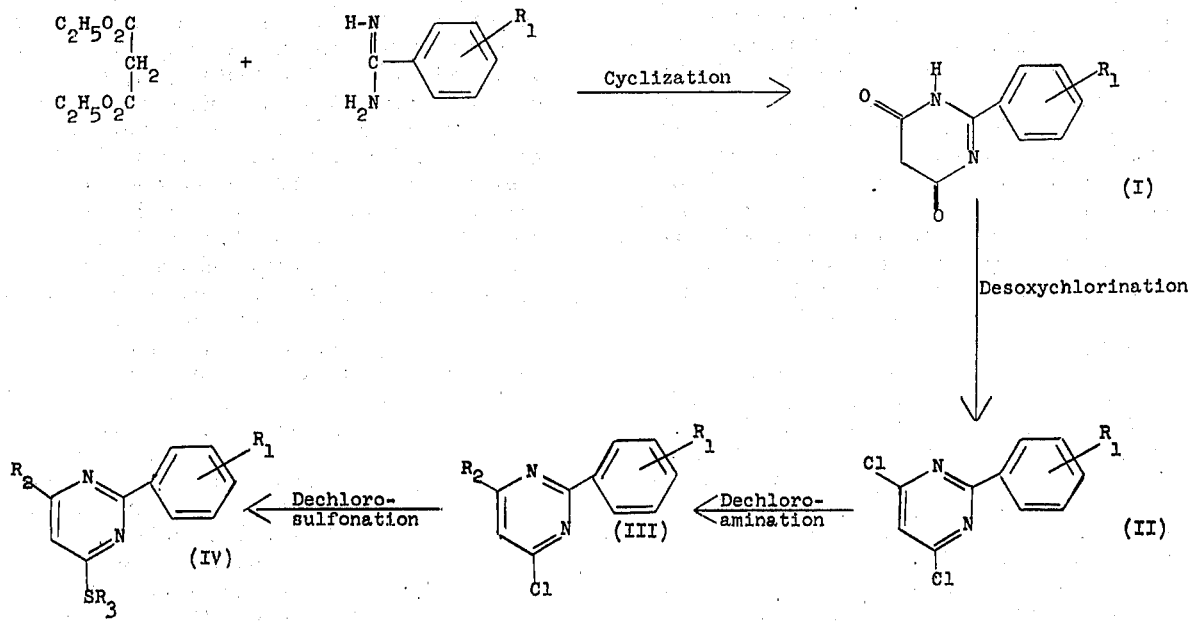

This invention relates to new and novel pyrimidine compounds. In particular, the present invention is concerned with 4-amino-2-phenyl-6-thiopyrimidine compounds having pharmacodynamic activity.

The novel compound which are included within the scope of this invention are represented by the following formula:

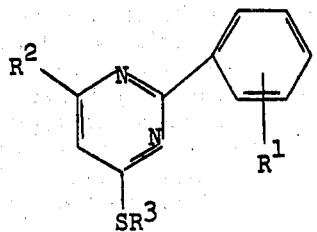

wherein $R^1$ is selected from the group consisting of hydrogen, dichloro, halogen, lower alkyl and lower alkoxy; $R^2$ is selected from the group consisting of amino, morpholinoethylamino, morpholinopropylamino, 4-(lower)alkylpiperazino, methoxyethylamino, methoxypropylamino, 4-hydroxyethylpiperazino, hydroxy(lower)alkylamino, lower alkoxycarbonylmethylamino, lower alkanoylamino(lower) alkylamino, hexahydroazepinyl, di(lower) alkylamino (lower)alkylamino, di(lower)alkoxyethylamino, and lower alkylamino; and $R^3$ is selected from the group consisting of phenyl, halophenyl, lower alkylphenyl, lower alkoxyphenyl, benzyl, halobenzyl, lower alkylbenzyl and lower alkoxybenzyl.

Specific examples of such compounds include: 4-(4-methyl-1-piperazinyl)-2-phenyl-6-phenylthiopyrimidine; 4-amino-6-(4-chlorophenylthio)-2-phenylpyrimidine; 4-(4-chlorophenylthio)-6-[2-(morpholinoethyl)amino]-2-phenylpyrimidine and 4-(4-chlorophenylthio)-6-(2-methoxyethylamino)-2-(4-tolyl)-pyrimidine.

The novel compounds of the present invention may be prepared as illustrated in the following reaction scheme:

wherein $R_1$, $R_2$ and $R_3$ are defined as above. The cyclization reaction between the commercially available diethyl malonate and an appropriate benzamidine is effected by refluxing a substantially equimolar mixture of these reactants in a reaction-inert solvent, such as ethanol, in the presence of sodium metal for a period of about two to about five hours. After the reaction is complete, the reaction mixture is filtered, the filter cake dissolved in water and precipitated by acidification to afford a 2-phenyl-4,6-(1H,5H)-pyrimidinedione (I).

The above prepared 2-phenyl-4,6-(1H,5H)-pyrimidinedione (I) is then admixed with phosphoryl chloride and slowly combined with N,N-diethylaniline. The reaction mixture is then heated to about reflux temperatures for a period of about three hours. Thereafter, the resulting 4,6-dichloro-2-phenylpyrimidine (II) is separated by conventional recovery procedures, e.g. concentration and recrystallization from a suitable solvent, such as ethanol.

The dechloroamination of a 4,6-dichloro-2-phenylpyrimidine (II) is performed by admixing a 4,6-dichloro-2-phenylpyrimidine with an amine and heating the resulting mixture until the reaction is complete. Thereafter, the resulting 4-amino-6-chloro-2-phenylpyrimidine (III) is obtained by conventional separation methods, such as, admixture with water and recrystallization of the resulting precipitate from an appropriate solvent, e.g. an alkanol, an alkane, benzenepetroleum ether mixtures and benzene.

The 4-amino-2-phenyl-6-thiopyrimidines (IV) of this invention are then prepared by the dechlorosulfonation of an appropriate 4-amino-6-chloro-2-phenylpyrimidine (III). This reaction is effected by admixing a 4-amino-6-chloro-2-phenylpyrimidine (III) with an excess amount of benzylmercaptan or thiophenol for a period of about fifteen minutes to about 5 hours at about 160°C. or at reflux temperatures. When the reaction is complete, the reaction mixture is basified by the addition of an alkali metal hydroxide and the 4-amino-2-phenyl-6-thiopyrimidine (IV) separated by routine procedures, e.g. crystallization, filtration and recrystallization from a suitable organic solvent, e.g. cyclohexane, n-heptane, benzenepetroleum ether, ethanol, methanol, ethanol-heptane, and dimethylformamide.

Many of the benzamidines, the 2-phenyl-4,6-(1H,5H)-pyrimidinediones (I), 4,6-dichloro-2-phenylpyrimidines (II), and the 6-amino-4-chloro-2-phenylpyrimidines (III) utilized in the synthesis of the compounds of the present invention are known compounds. Others which have not previously been known are prepared in accord with the aforesaid reaction sequence, specific illustration thereof is hereinafter given in the Examples.

In accord with the present invention, the new 4-amino-2-phenyl-6-thiopyrimidines (IV) herein described have been found to possess interesting pharmaceutical properties which render them useful as synthetic medicinals. More particularly, these compounds, in standard pharmacological tests, have exhibited utility as central nervous system depressants. That is they produce a calming effect in the host.

In the pharmacological evaluation of the biological actitity of the compounds of this invention, the in vivo effects are tested as follows. The compound is administered orally or intraperitoneally to three mice (14 to 24 grams) at each of the following doses: 400, 127, 40 and 12.7 milligrams per kilogram of host body weight (MPK). The animals are watched for a minimum of two hours during which time signs of general stimulation, (i.e., increased spontaneous motor activity, hyperactivity on tactile stimulation, twitching), general depression (i.e., decreased spontaneous motor activity, decreased respiration), autonomic activity (i.e., miosis, mydriasis, diarrhea) are noted.

Many of the compounds of this invention when tested in the foregoing pharmacological evaluation induced central nervous system depressant effects at a dose of 12.7 to 400 MPK. The specific results of testing with individual compounds is stated below in the examples. Because the compounds are similar in structure, it is expected that the compounds which showed no activity at 400 MPK would show a central nervous system depressant activity at higher doses. This is expected because the differences between the compounds are in parts of the molecule which would reasonably be expected to affect the degree of activity rather that the presence or absence of activity. Moreover, the compounds that showed no central nervous system activity at a dosage of 400 MPK did show other activities. For instance the compound 4-(4-methyl-1-piperazinyl)-2-phenyl-6-phenylthiopyrimidine showed antiamebic activity with a 64 to 76% kill in a standard pharmacological antiamebic evaluation. The compound 4-(p-chlorophenylthio)-6-[(2-methoxyethyl)amino]-2-phenylpyrimidine which showed no central nervous system activity at a dose of 400 MPK showed an antagonism to reserpine ptosis when tested in a standard pharmacological evaluation. The compound 4-[4-(p-chlorophenylthio)-2-phenyl-6-pyrimidinyl]-1-piperazine ethanol which showed no central nervous system activity at a dosage of 400 MPK showed anti-convulsive properties at a dosage of 127.1 MPK in a standard pharmacological evaluation.

When the compounds of this invention are employed as described above, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as starch, milk, sugar, certain types of clay and so forth. They may be administered sublingually in the form of troches or lozenges in which the active ingredient is mixed with sugar and corn syrups; and then dehydrated sufficiently to make it suitable for pressing into a solid form. They may be administered orally in the form of solutions which may contain coloring and flavoring agents or they may be injected parenterally, that is intramuscularly, intravenously or subcutaneously. For parenteral administration they may be used in the form of a sterile solution containing other solutes, for example enough saline or glucose to make the solution isotonic. The dosage of the present therapeutic agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

In order more clearly to disclose the nature of the present invention, specific examples of the practice of the invention are hereinafter given. It should be understood, however, that this is done solely by way of example and is intended neither to delineate the scope of the invention nor limit the ambit of the appended claims. In the examples all temperatures are stated in degrees Centigrade, and the following abbreviations are used: "g." for grams, "ml." for milliliters, and "mole" for grams molecular weight.

EXAMPLE I

To a stirred solution of 35.8 g. of sodium metal in one liter of absolute ethanol, there is added 88.5 g. of m-toluamidine hydrochloride followed by the dropwise addition of 91.5 g. of diethyl malonate over a fifteen minutes period. The reaction mixture is heated under reflux for four hours. The solution is filtered and the filter cake dissolved in water. The ethanol filtrate is evaporated to dryness and the solid residue added to the water solution. Upon acidification of the aqueous solution to $pH_2$ with concentrated hydrochloric acid, a solid separates which is removed by filtration. After washing this material several times with water, the product is recrystallized from aqueous N,N-dimethylformamide to afford 2-(3-tolyl)-4,6-(1H,5H)-pyrimidinedione, m.p. 247.5°c.

Anal. for $C_8H_{10}N_2O_2$: Calcd. C, 65.33; H, 4.98; N, 13.86. Found: C, 65.26; H, 5.18; N, 13.68.

To a mixture of 108 g. of the above prepared 2-(3-tolyl)-4,6-(1H,5H)-pyrimidinedione in 700 ml. of phosphoryl chloride there is slowly added 80 g. of N,N-diethylaniline. The reaction mixture is heated with stirring under reflux for three hours, then evaporated to dryness in vacuo on a rotary evaporator, and ice is added to the residual oil. The dark brown solid which results is recrystallized from ethanol affording 82.3 g. of product, m.p. 76°–78°C., which when recrystallized from ethanol yields 4,6-dichloro-2-(3-tolyl)-pyrimidine, m.p. 80-81°C.

Anal. for $C_{11}H_8Cl_2N_2$: Calcd. C, 55.24; H, 3.37; N, 11.72; Cl, 29.6. Found: C, 55.24; H, 3.62; N, 11.57; Cl, 29.4.

Similarly, reacting p-toluamidine hydrochloride with diethyl malonate affords 2-(4-tolyl)-4,6-(1H,5H)-pyrimidinedione which is then reacted with phosphoryl chloride to produce 4,6-dichloro-2-(4-tolyl)-pyrimidine, m.p. 84°–85°C.

Anal. for $C_{11}H_8Cl_2N_2$: Calcd. C, 55.24; H, 3.37; N, 11.72; Cl, 29.6. Found: C, 55.29; H, 3.51; N, 11.44; Cl, 29.6.

EXAMPLE II

To a stirred solution of 56.4 g. of sodium metal in one liter of absolute ethanol there is added 156 g. of m-chlorobenzamidine hydrochloride followed by the dropwise addition of 144 g. of diethyl malonate over a fifteen minutes period. The reaction mixture is heated under reflux for three hours. The solution is filtered and the filter cake dissolved in water. The ethanol filtrate is evaporated to dryness and the solid residue added to the water solution. Upon acidification of the aqueous solution to $pH_2$ with concentrated hydrochloric acid, a solid separates which is removed by filtration. After washing this material several times with water the product (123 g., m.p. 254°–256°C.) is recrystallized from aqueous N,N-dimethylformamide to yield 2-(3-chlorophenyl)-4,6-(1H,5H)-pyrimidinedione, m.p. 256°–257°C.

Anal. for $C_{10}H_7N_2O_2Cl$: Calcd. C, 53.95; H, 3.17; N, 12.59; Cl, 15.93 Found: C, 53.88; H, 3.18; N, 12.57; Cl, 15.65.

To a mixture of the above prepared 2-(3-chlorophenyl)-4,6-(1H,5H)-pyrimidinedione (120.9 g.) in 500 ml. of phosphoryl chloride there is added slowly 161 g. of N,N-diethylaniline. The reaction mixture is evaporated to dryness in vacuo on a rotary evaporator and ice is added to the residual oil. The dark brown solid which results is recrystallized from ethanol affording 4,6-dichloro-2-(3-chlorophenyl)-pyrimidine, m.p. 118°–119.5°C.

Anal. for $C_{10}H_5N_2Cl_3$: Calcd. C, 46.28; H, 1,94; N, 10.8; Cl, 40.98. Found: C, 46.30; H, 2.15; N, 10.8; Cl, 40.8.

In a similar manner, reacting p-bromobenzamidine hydrobromide with diethyl malonate produces 2-(4-bromophenyl)-4,6-(1H,5H)-pyrimidinedione, which is reacted with phosphoryl chloride to afford 2-(4-bromophenyl)-4,6-dichloropyrimidine.

EXAMPLE III

Employing the procedure of Example II to react 97.6 g. of p-methoxybenzamidine hydrochloride and 92.4 g. of diethyl malonate in 1500 ml. of absolute ethanol, in the presence of 36.2 g. of sodium metal, there is produced 2-(4-methoxyphenyl)-4,6-(1H,5H)-pyrimidinedione, m.p. 299°–300°C. (dec.).

Anal. for $C_{11}H_{10}N_2O_3$: Calcd. C, 60.54; H, 4.62; N, 12.84. Found: C, 60.83; H, 4.98; N, 12.95.

In a similar manner, the interaction of 73.1 g. of o-toluamidine hydrochloride with 75.5 g. of diethyl malonate in one liter of absolute ethanol containing 29.6 g. of sodium affords 2-(2-tolyl)-4,6-(1H,5H)-pyrimidinedione, m.p. 319°–320°C.

Anal. for $C_{11}H_{10}N_2O_2$: Calcd. C, 65.33; H, 4.98; N, 13.86. Found: C, 65.53; H, 5.22; N, 13.58.

A mixture of 66.5 g. of the above prepared 2-(2-tolyl)-4,6-(1H,5H)-pyrimidinedione in 400 ml. of phosphoryl chloride is reacted with 49.2 g. of N,N-diethylaniline. Recrystallization of the product from ethanol affords 58.4 g. of 4,6-dichloro-2-(2-tolyl)-pyrimidine, m.p. 76.5°–77°C.

EXAMPLE IV 3,4-Dichlorophenylamidine hydrochloride (22.5 g.) is added with stirring to a solution of sodium (6.9 g.) in absolute ethanol (120 ml.) followed by the dropwise addition of diethyl malonate (22.2 g.) over a thirty minutes period. The reaction mixture is heated under reflux for three hours and then filtered. The filter cake is dissolved in water. The ethanol filtrate is evaporated to dryness and the solid residue added to the water solution. Upon acidification of the aqueous solution of $pH_2$ with concentrated hydrochloric acid, a solid precipitates which is removed by filtration. After washing this material with water the product (21.5 g., m.p. 310°–315°C.) is recrystallized from N,N-diemthylformamide to afford 2-(3,4-dichlorophenyl)-4,6-(1H,5H)-pyrimidinedione, m.p. 315°–317°C. (dec.).

A mixture of 19.45 g. of the above prepared 2-(3,4-dichlorophenyl)-4,6-(1H,5H)-pyrimidinedione in 70 ml. of phosphoryl chloride there is added 11.3 g. of N,N-diethylaniline as in Example I. Recrystallization of the product from n-heptane affords 19.8 g. of 4,6-dichloro-2-(3,4-dichlorophenyl)-pyrimidine, 122°–124°C.

Anal. for $C_{10}H_6N_2Cl_4$: Calcd. C, 40.85; H, 1.37; N, 9.53; Cl, 48.24. Found: C, 41.02; H, 1.38; H, 9.82; Cl, 48.2.

EXAMPLE V

To a stirred solution of 56.4 g. of sodium metal in one liter of absolute ethanol there is added 156 g. of p-chlorobenzamidine hydrochloride followed by the dropwise addition of 144 g. of diethyl malonate over a thirty minutes period. The reaction mixture is heated under reflux for five hours. The solution is filtered and the filter cake is dissolved in water. The ethanol filtrate is evaporated to dryness and the solid residue added to the water solution. Upon acidification of the aqueous solution to $pH_2$ with concentrated hydrochloric acid, a solid precipitates which is removed by filtration. Washing this material several times with water affords 2-(4-chlorophenyl)-4,6-(1H,5H)-pyrimidinedione.

To a mixture of 127 g. of the above prepared 2-(4-chlorophenyl)-4,6-(1H,5H)-pyrimidinedione in 700 ml. of phosphoryl chloride there is added slowly 171 g. of N,N-diethylaniline. The reaction mixture is heated with stirring under reflux for three hours. The reaction mixture is evaporated to dryness in vacuo on a rotary evaporator and ice is added to the residual oil. The dark brown solid which results is recrystallized from ethanol affording 82.4 g. of 4,6-dichloro-2-(4-chlorophenyl)-pyrimidine, m.p. 120°–121°C.

EXAMPLE VI

Repeating the procedure of Examples I to IV to react an appropriate amidine with diethyl malonate, the following pyrimidinediones are obtained which are then reacted with phosphoryl chloride to form the hereinafter listed dichloropyrimidines:

| Pyrimidinediones | Dichloropyrimidines |
| --- | --- |
| 2-(4-ethylphenyl)-4,6-(1H,5H)-pyrimidinedione | 4,6-dichloro-2-(4-ethylphenyl)-pyrimidine |
| 2-(3-fluorophenyl)-4,6-(1H,5H)-pyrimidinedione | 4,6-dichloro-2-(3-fluorophenyl)-pyrimidine |
| 2-(4-propoxyphenyl)-4,6-(1H,5H)-pyrimidinedione | 4,6-dichloro-2-(4-propoxyphenyl)-pyrimidine |
| 2-phenyl-4,6-(1H,5H)-pyrimidinedione. | 4,6-dichloro-2-phenylpyrimidine. |

EXAMPLE VII

Six grams of 4,6-dichloro-2-phenylpyrimidine is added in small portions to 25 ml. of N-($\beta$-aminoethyl)-morpholine with slight warming and stirring. An exothermic reaction takes place during the addition. The resulting mixture is heated on a steam bath for several minutes and then poured into 500 ml. of water. The semisolid product thus obtained is recrystallized from benzene and petroleum ether using declorizing charcoal to give 5.0 g. of 4-chloro-6-[2-(morpholino)ethylamino]-2-phenylpyrimidine, m.p. 80°–82°C.

Anal. for $C_{16}H_{19}N_4OCl$: Calcd. C, 60.28; H, 6.01; N, 17.58. Found: C, 60.36; H, 6.03; N, 17.87.

A well blended mixture of 2.7 g. of the above prepared 4-chloro-6-[2-(morpholino)ethylamino]-2-phenylpyrimidine and 6.3 g. of p-chlorothiophenol is heated in an oil bath maintaining the temperature at 160°C. for 3 hours. After being cooled to room temperature, the reaction mixture is triturated with 60 ml. of 30% sodium hydroxide. The product is collected on a sintered glass funnel and washed with water repeatedly to yield 3.7 g. of product. Upon recrystallization from ethanol, there is obtained 4-(4-chlorophenylthio)-6-[2-(morpholinoethyl)amino]-2-phenylpyrimidine, m.p. 171°–173°C.

Anal. for $C_{22}H_{23}N_4SOCl$: Calcd. C, 61.89; H, 5.40; N, 13.12; S, 7.51; Cl, 8.30. Found: C, 61.73; H, 5.36; N, 13.39; S, 7.7; Cl, 8.3.

Similarly, 2-(4-bromophenyl)-4,6-dichloropyrimidine is reacted with N-(3-aminopropyl)-morpholine to afford 2-(4-bromophenyl)-4-chloro-6-[3-(morpholino)propylamino]pyrimidine which is then reacted with p-chlorothiophenol to produce 2-(4-bromophenyl)-4-(4-chlorophenylthio)-6-[3-(morpholinopropyl)amino]-pyrimidine.

EXAMPLE VIII

Two grams of 4,6-dichloro-2-phenylpyrimidine is added in small portions to 10 ml. of N-methylpiperazine with slight warming and stirring. The resulting mixture is heated on a steam bath for several minutes, then poured into 250 ml. of water. The product (2.4 g., m.p. 81°–87°C.) is then recrystallized from n-pentane to afford 4-chloro-6-(4-methyl-1-piperazinyl)-2-phenylpyrimidine, m.p. 91°–92.5°C.

Anal. for $C_{15}H_{17}N_4Cl$: Calcd. C, 62.38; H, 5.93; N, 19.40; Cl, 12.28. Found: C, 62.32; H, 5.65; N, 19.62; Cl, 12.1.

A mixture of 3.0 g. of the above prepared 4-chloro-6-(4-methyl-1-piperazinyl)-2-phenylpyrimidine and 10 ml. of thiophenol is heated under reflux for three hours and then poured into 300 ml. of water. The reaction mixture is basified with 40% sodium hydroxide solution. The product which is deposited crystallizes on cooling to afford 3.5 g. of product. Recrystallization from n-heptane affords 4-(4-methyl-1-piperazinyl)-2-phenyl-6-phenylthiopyrimidine, m.p. 125°–128°C.

Anal. for $C_{21}H_{22}N_4S$: Calcd. C, 69.58; H, 6.12; N, 15.46; S, 8.85. Found: C, 69.49; H, 6.13; N, 15.42; S, 8.6.

Similarly, 4-(4-ethyl-1-piperazinyl)-2-phenyl-6-phenylthiopyrimidine is produced.

EXAMPLE IX

Seven grams of 4,6-dichloro-2-phenylpyrimidine is added in small portions to 30 ml. of $\beta$-methoxyethylamine with slight warming and stirring. The resulting mixture is heated on a steam bath for several minutes and then poured into 500 ml. of water. The product thus obtained (5.1 g.) is recrystallized from n-heptane to afford 4-chloro-6-(2-methoxyethylamino)-2-phenylpyrimidine, 48.5°–50°C.

Anal. for $C_{13}H_{14}N_3OCl$: Calcd. C, 59.21; H, 5.35; N, 15.93. Found: C, 59.32; H, 5.31; N, 15.72.

A well blended mixture of 4.3 g. of 4-chloro-6-(2-methoxyethylamino)-2-phenylpyrimidine and 10.0 g. of p-chlorothiophenol is heated in an oil bath maintaining the temperature at 160°C. for 3 hours. After being cooled to room temperature, the reaction mixture is triturated with 60 ml. of 30% sodium hydroxide. The product is collected on a sintered glass funnel and washed with water repeatedly. Two recrystallizations of the crude product affords 2.0 g. of 4-(4-chlorophenylthio)-6-[(2-methoxyethyl)amino]-2-phenylpyrimidine, m.p. 128°–130°C.

Anal. for $C_{19}H_{18}N_3SOCl$: Calcd. C, 61.36; H, 4.88; N, 11.30; S, 8.62; Cl, 9.54. Found: C, 61.10; H, 4.81; N, 11.59; S, 8.9; Cl, 9.75.

In the same manner, 4,6-dichloro-2-phenylpyrimidine is reacted with 3-methoxypropylamine to produce 4-chloro-6-(3-methoxypropylamino)-2-phenylpyrimidine, which is then reacted with p-chlorothiophenol to afford 4-(4-chlorophenylthio)-6-[(3-methoxypropyl)amino]-2-phenylpyrimidine.

EXAMPLE X

N-hydroxyethylpiperazine (7.81 g.) diluted with 20 ml. of absolute ethanol is added to a slurry obtained by adding 6.75 g. of 4,6-dichloro-2-phenylpyrimidine to 25 ml. of absolute ethanol. The resulting mixture is refluxed for fifteen minutes, then poured into 850 ml. of water. A gummy material which separates solidifies on standing overnight. The crude product weighs 7.8 g. which is recrystallized from n-heptane to afford 4-(4-chloro-2-phenylpyrimidin-6-yl)-1-piperazineethanol, m.p. 103°–105°C.

Anal. for $C_{16}H_{19}N_4OCl$: Calcd. C, 60.28; H, 6.01; N, 17.58. Found: C, 60.08; H, 5.70; N, 17.48.

A well blended mixture of 3.8 g. of 4-(4-chloro-2-phenylpyrimidin-6-yl)-1-piperazineethanol and 7.0 g. of p-chlorothiophenol is heated in an oil bath maintaining the temperature at 160°C. for 3 hours. After being cooled to room temperature, the reaction mixture is triturated with 60 ml. of 30°/o sodium hydroxide. The product is collected on a sintered glass funnel and washed with water repeatedly. Upon recrystallization from 65°/o ethanol, there is obtained 4-[4-(4-chlorophenylthio)-2-phenyl-6-pyrimidinyl]-1-piperazine ethanol, m.p. 118°–120°C.

Anal. for $C_{22}H_{23}N_4SOCl$: Calcd. C, 61.89; H, 5.43; N, 13.12; S, 7.51; Cl, 8.31. Found: C, 61.80; H, 4.95; N, 12.76; S, 7.5; Cl, 8.29.

EXAMPLE XI

To a solution of 1.2 g. of sodium in 50 ml. of ethanol, there is added 8.4 g. of ethyl glycinate hydrochloride and 6.7 g. of 4,6-dichloro-2-phenylpyrimidine. The reaction mixture is heated with stirring for 2 hours under reflux then taken to dryness on a rotary evaporator. After the addition of 200 ml. of water the residue which is deposited amounts to 8.5 g., m.p. 83°–132°C. Recrystallization from benzene yields 8.3 g. of N-(6-chloro-2-phenyl-4-pyrimidinyl)glycine, ethyl ester, m.p. 147°–149°C.

Anal. for $C_{14}H_{14}N_3O_2Cl$: Calcd. C, 57.64; H, 4.84; N, 14.40; Cl, 12.15. Found: C, 57.66; H, 4.85; N, 14.59; Cl, 12.2.

A mixture of the above prepared N-(6-chloro-2-phenyl-4-pyrimidinyl)-glycine, ethyl ester is reacted with thiophenol, as in Example X, to afford N-(2-phenyl-6-phenylthio-4-pyrimidinyl)-glycine, ethyl ester.

In a similar manner, N-[2-(4-chlorophenyl)-6-phenylthio-4-pyrimidinyl]-glycine, propyl ester and N-(2-phenyl-6-phenylthio-4-pyrimidinyl)-glycine, ethyl ester are prepared.

EXAMPLE XII

Six grams of 4,6-dichloro-2-phenylpyrimidine is added in small portions to 10 ml. of hexamethyleneimine with slight warming and stirring. The resulting mixture is heated on a steam bath for several minutes, then poured into 500 ml. of water. The product (7.56 g., 62°–64°C.) thus obtained is recrystallized from n-heptane affords 4-chloro-6-(hexahydroazepin-1-yl)-2-phenylpyrimidine, m.p. 64°–66°C.

Anal. for $C_{16}H_{18}N_3Cl$: Calcd. C, 66.77; H, 6.30; N, 14.60. Found: C, 66.80; H, 6.37; N, 14.26.

A mixture of the above prepared 4-chloro-6-(hexahydroazepin-1-yl)-2-phenylpyrimidine is reacted with p-chlorothiophenol, as in Example X, to produce 4-(4-chlorophenylthio)-6-(hexahydroazepin-1-yl)-2-phenylpyrimidine.

EXAMPLE XIII

Employing the procedure of Example VII, 7.0 g. of 4,6-dichloro-2-(p-chlorophenyl)-pyrimidine and 30 ml. of N-(β-aminoethyl)-morpholine is reacted to produce 8.9 g. of product. Recrystallization from n-heptane affords 4-chloro-2-(4-chlorophenyl)-6-[2-(morpholino)ethylamino]-pyrimidine, m.p. 127°–129°C.

Anal. for $C_{16}H_{18}N_4Cl_2$: Calcd. C, 54.40; H, 5.14; N, 15.86; Cl, 20.07. Found: C, 54.50; H, 4.89; N, 16.08; Cl, 19.70.

Reacting 6.0 g. of 4-chloro-2-(4-chlorophenyl)-6-[2-(morpholino)ethylamino]-pyrimidine with 14.0 g. of p-chlorothiophenol yields 4.3 g. of product. Two recrystallizations from absolute ethanol afford 2-(4-chlorophenyl)-4-(4-chlorophenylthio)-6-[2-(morpholino)ethylamino]-pyrimidine, m.p. 159°–161°C.

Anal. for $C_{22}H_{22}N_4SOCl_2$: Calcd. C, 57.26; H, 4.81; N, 12.14; S, 6.95; Cl, 15.37. Found: C, 57.23; H, 4.64; N, 12.27; S, 7.0; Cl, 15.3.

Similarly, 4-chloro-2-(4-chlorophenyl)-6-[3-(morpholino)propylamino]-pyrimidine is reacted with p-ethylthiophenol to produce 2-(4-chlorophenyl)-4-(4-ethylphenylthio)-6-[3-(morpholino)propylamino]-pyrimidine.

EXAMPLE XIV

Seven grams of 4,6-dichloro-2-(p-chlorophenyl)-pyrimidine is added in small portions to 30 ml. of β-methoxyethylamine with slight warming and stirring. The resulting mixture is heated on a steam bath for several minutes, then poured into 500 ml. of water. The product thus obtained is recrystallized from n-heptane to give 5.6 g. of 4-chloro-2-(4-chlorophenyl)-6-[2-(methoxyethyl)amino]-pyrimidine, m.p. 64°–65°C.

Anal. for $C_{13}H_{13}N_3OCl$: Calcd. C, 52.37; H, 4.39; N, 14.09. Found: C, 52.42; H, 4.56; N, 13.75.

A well blended mixture of 7.0 g. of the above prepared pyrimidine and 16.3 g. of p-chlorothiophenol is heated in an oil bath maintaining the temperature at 160°C. for 3 hours. After being cooled to room temperature, the reaction mixture is triturated with 60 ml. of 30°/o sodium hydroxide. The product is collected on a sintered glass funnel and washed with water repeatedly. Two recrystallizations from n-heptane afford 3.0 g. of 2-(4-chlorophenyl)-4-(4-chlorophenylthio)-6-[(2-methoxyethyl)amino]-pyrimidine, m.p. 135°–138°C.

Anal. for $C_{19}H_{17}N_3SOCl_2$: Calcd. C, 56.16; H, 4.22; N, 10.34; S, 7.89; Cl, 17.45. Found: C, 56.21; H, 4.13; N, 10.6; S, 7.9; Cl, 17.3.

Similarly, 4,6-dichloro-2-(3-chlorophenyl)-pyrimidine is reacted with β-methoxyethylamine to produce 4-chloro-2-(3-chlorophenyl)-6-[2-(methoxyethyl)-amino]-pyrimidine (m.p. 75°–76°C.) which is then reacted with p-fluorothiophenol to afford 2-(3-chlorophenyl)-4-(4-fluorophenylthio)-6-[(2-methoxyethyl)-amino]pyrimidine.

EXAMPLE XV

Two grams of 4,6-dichloro-2-phenylpyrimidine is added in small portions to 10 ml. of N-methylpiperazine with slight warming and stirring. An exothermic reaction takes place during the addition. The resulting mixture is heated on a steam bath for several minutes and then poured into 250 ml. of water. The product thus obtained is recrystallized from n-pentane to afford 4-chloro-6-(4-methyl-1-piperazinyl)-2-phenylpyrimidine, m.p. 91°–92.5°C.

A well blended mixture of the above prepared 4-chloro-6-(4-methyl-1-piperazinyl)-2-phenylpyrimidine (2.0 g.) and 5.0 g. of p-chlorothiophenol is heated in an oil bath maintaining the temperature at 160°C. for 3 hours. After being cooled to room temperature, the reaction mixture is triturated with 60 ml. of 30°/o sodium hydroxide. The product is collected on a sintered glass funnel and washed with water repeatedly. It amounted to 2.9 g. and melted at 145°–150°C. Upon recrystallization from absolute ethanol, there is obtained 4-(4-chlorophenylthio)-6-(4-methyl-1- piperazinyl)-2-phenylpyrimidine, m.p. 152°–154°C.

Anal. for $C_{21}H_{21}N_4SCl$: Calcd. C, 63.54; H, 5.33; N, 14.12; S, 8.08. Found: C, 63.78; H, 5.60; N, 14.07; S, 8.1.

The latter compound when evaluated in the foregoing pharmacological procedure showed decreased motor activity at a dosage of 12.7 MPK and decreased respiration at a dosage of 40 MPK.

In a similar manner, the following intermediates are prepared which are then reacted with an appropriate thiophenol to afford the hereinafter listed products:

| INTERMEDIATES | PRODUCTS |
| --- | --- |
| 6-chloro-2-(3-chlorophenyl)-4-[2-(dimethylamino)ethylamino]-pyrimidine, m.p. 77–78.5°C. | 2-(3-chlorophenyl)-4-(4-chlorophenylthio)-6-[(2-dimethylamino)ethylamino]-pyrimidine, m.p. 108–109.5°C. |
| 2-[4-chloro-2-(4-methoxyphenyl)-6-pyrimidinylamino]-ethanol, m.p. 133–134.5°C. | 2-[2-(4-methoxyphenyl)-4-phenylthio-6-pyrimidinylamino]-ethanol |

| Intermediates | Products |
| --- | --- |
| 4-[4-chloro-2-(4-methoxyphenyl)-pyrimidin-6-yl]-1-piperazineethanol, m.p. 113–114°C. | 4-[4-(4-chlorophenylthio)-2-(4-methoxyphenyl)-pyrimidin-6-yl]-1-piperazineethanol |
| 4-chloro-6-[2-(dimethylamino)ethylamino]-2-(4-tolyl)-pyrimidine, m.p. 64–66.5°C. | 4-(4-chlorophenylthio)-6-[2-(dimethylamino)ethylamino]-2-(4-tolyl)-pyrimidine, m.p. 136.5–138.5°C. |
| 6-chloro-2-(4-fluorophenyl)-4-[4-(dimethylamine)butylamino]-pyrimidine | 2-(4-fluorophenyl)-6-[4-dimethylamino)butylamino]-4-(4-tolylthio)-pyrimidine |
| 3-[4-chloro-2-(4-methoxyphenyl)-6-pyrimidinylamino]-propanol. | 3-[2-(4-methoxyphenyl)-4-phenylthio-6-pyrimidinylamino]-propanol. |

EXAMPLE XVI

Seven grams of 4,6-dichloro-2-(3,4-dichlorophenyl)-pyrimidine is added in small portions to 25 ml. of N,N-dimethylethylenediamine with slight warming and stirring. The resulting mixture is heated on a steam bath for several minutes then poured into 500 ml. of water. The product thus obtained is recrystallized from n-heptane to afford 4-chloro-2-(3,4-dichlorophenyl)-6-[2-(dimethylamino)ethylamino]-pyrimidine, m.p. 99.5°–102°C.

Anal. for $C_{14}H_{15}N_4Cl_3$: Calcd. C, 48.64; H, 4.37; N, 16.21; Cl, 30.77. Found: C, 48.69; H, 4.38; N, 15.96; Cl, 30.7.

The above prepared pyrimidine is reacted with p-chlorothiophenol to obtain a product which is repeatedly recrystallized from cyclohexane to afford 4-(4-chlorophenylthio)-2-(3,4-dichlorophenyl)-6-[2-(dimethylamino)ethylamino]-pyrimidine ½ cyclohexane, m.p. 99°–103°C.

Anal. for $C_{20}H_{19}Cl_3N_4S$ . ½ cyclohexane: Calcd. C, 55.70; H, 5.08; N, 11.30; S, 6.47; Cl, 21.45. Found: C, 55.47; H, 4.92; N, 11.53; S, 6.5; Cl, 21.8.

Similarly, 7.0 g. of 4,6-dichloro-2-(p-chlorophenyl)-pyrimidine and 30 ml. of N,N-dimethyl-ethylenediamine are reacted followed by reaction of the crude product with 15 g. of p-chlorothiophenol. The product (8.0 g.) is recrystallized from heptane and then from absolute ethanol to afford 2-(4-chlorophenyl)-6-(4-chlorophenylthio)-4-[2-dimethylaminoethyl)amino]-pyrimidine, m.p. 98°–100°C.

Anal. for $C_{20}H_{20}N_4SCl_2$: Calcd. C, 57.18; H, 4.81; N, 13.36; S, 7.65. Found: C, 57.46; H, 4.76; N, 13.62; S, 7.7.

EXAMPLE XVII

A solution of 7.2 g. of f 4,6-dichloro-2-p-tolyl)-pyrimidine and 7.8 g. of N-hydroxyethylpiperazine in 35 ml. of absolute ethanol is refluxed for fifteen minutes. Pouring of the resulting solution into 700 ml. of water causes separation of a gummy material which solidifies on standing. The crude product weighs 8.7 g. and recrystallization from n-heptane affords 4-[4-chloro-2-(4-tolyl)-6-pyrimidinyl]-1-piperazine ethanol, m.p. 103.5°–104.5°C.

Anal. for $C_{17}H_{21}N_4OCl$: Calcd. C, 61.34; H, 6.36; N, 16.83; Cl, 10.65. Found: C, 61.17; H, 6.07; N, 17.07; Cl, 10.7.

A well blended mixture of 4.3 g. of the above prepared compound and 9.0 g. of p-chlorothiophenol is heated in an oil bath maintaining the temperature at 160°C. for one half hour. After being cooled to room temperature, the reaction mixture is triturated with 60 ml. of 30°/o sodium hydroxide. The product is collected on a sintered glass funnel and washed with water repeatedly. In this manner, is obtained 4-[4-(4-chlorophenylthio)-2-(4-tolyl)-pyrimidin-6-yl]-1-piperazineethanol, m.p. 123°–125°C.

Anal. for $C_{23}H_{25}N_4SOCl$: Calcd. C, 62.64; H, 5.71; N, 12.71; S, 7.27; Cl, 8.04. Found: C, 62.57; H, 5.90; N, 12.83; S, 7.3; Cl, 8.04.

Similarly, 4-[4-(4-bromophenylthio)-2-(4-propylphenyl)-pyrimidin-6-yl]-1-piperazineethanol is synthesized.

EXAMPLE XVIII

A solution of 7.2 g. of 4,6-dichloro-2-(p-tolyl)pyrimidine and 4.5 g. of β-methoxyethylamine in 35 ml. of absolute ethanol is refluxed for 15 minutes. Pouring of the resulting solution into 700 ml. of water causes separation of a gummy material which solidifies on standing. The crude product weighs 7.3 g. and recrystallization from n-heptane affords 4-chloro-6-[2-(methoxy)ethylamino]-2-(4-tolyl)pyrimidine, 70°–72°C.

Anal. for $C_{14}H_{16}N_3OCl$: Calcd. C, 60.54; H, 5.81; N, 15.13; Cl, 12.61. Found: C, 60.41; H, 5.86; N, 15.27; Cl, 13.0.

A mixture of 4.3 g. of the above prepared compound and 7.0 g. of p-chlorothiophenol is heated in an Oil bath maintaining the temperature at 160°C. for 3 hours. After being cooled to room temperature, the reaction mixture is triturated with 60 ml. of 30°/o sodium hydroxide. The product is collected on a sintered glass funnel and washed with water repeatedly. Recrystallization of the crude product (6.7 g.) from aqueous ethanol 4-(4-chlorophenylthio)-6-(2-methoxyethylamino)-2-(4-tolyl)pyrimidine, m.p. 141°–144°C.

Anal. for $C_{20}H_{20}N_3SOCl$: Calcd. C, 62.24; H, 5.22; N, 10.89; S, 8.31; Cl, 9.19. Found: C, 62.08; H, 5.20; N, 11.01; S, 8.34; Cl, 9.62.

The latter compound when evaluated in the foregoing pharmacological procedure showed decreased motor activity and decreased respiration in the host at a dosage of 127 MPK.

In a similar manner, 4,6-dichloro-2-(p-ethylphenyl)-pyrimidine is reacted with γ-methoxypropylamine to obtain 4-chloro-2-(4-ethylphenyl)-6-[3-(methoxy)propylamino]-pyrimidine which is then reacted with thiophenol to afford 2-(4-ethylphenyl)-6-(3-methoxypropylamino)-4-phenylthiopyrimidine.

EXAMPLE XIX

A blended mixture of 6.5 g of 4-chloro-6-(2-methoxyethylamino)-2-(4-methoxyphenyl)-pyrimidine and 15.0 g. of p-chlorothiophenol is heated to 160°C. for 3 hours. Thereafter, the reaction mixture is cooled to room temperature and triturated with 60 ml. of 30°/o sodium hydroxide. The product is separated by filtration, washed with water and recrystallized from absolute ethanol to afford 6-(4-chlorophenylthio)-4-(2-methoxyethylamino)-2-(4-methoxyphenyl)pyrimidine, m.p. 117°–118.5°C.

Anal. for $C_{20}H_{20}N_3SO_2CL$: Calcd. C, 59.77; H, 5.02; N, 10.45; S, 7.98. Found: C, 59.92; H, 5.08; N, 10.24; S, 7.96.

The latter compound when tested in the foregoing pharmacological evaluation showed decreased motor activity at a dosage of 40 MPK and decreased respiration at a dose of 127 MPK in the host.

In the above manner, the following products are obtained:

4-(4-chlorophenylthio)-2-(4-methoxyphenyl)-6-[(2-dimethylamino)ethylamino]-pyrimidine, m.p. 121°–122°C.;

2-(4-chlorophenyl)-4-(4-chlorophenylthio)-6-[2-diethylamino)ethylamino]-pyrimidine, m.p. 112°–114°C.;

N-[2-(6-[4-chlorophenylthio]-2-phenylpyrimidin-4-yl-amino)ethyl]-acetamide, m.p. 165°–166°C.; and 2-(4-chlorophenyl)-4-(4-chlorophenylthio)-6-(4-methylpiperazin-1-yl)-pyrimidine, m.p. 163°–165°C.

EXAMPLE XX

A solution of 7.8 g. of 4,6-dichloro-2-(m-chlorophenyl)-pyrimidine and 6.0 g. of N-methylpiperazine in 35 ml. of absolute ethanol is refluxed for fifteen minutes. Pouring of the resulting solution into 700 ml. of water causes separation of a gummy material which solidifies on standing over a weekend. The crude product weighs 6.5 g. and recrystallization from n-heptane affords cotton-like crystals of 4-chloro-2-(3-chlorophenyl)-6-(4-methylpiperazin-1-yl)-pyrimidine, m.p. 93°–94°C.

Anal. for $C_{15}H_{16}N_4Cl_2$: Calcd. C, 55.74; H, 4.99; N, 17.33. Found: C, 55.39; H, 5.28; N, 17.16.

A well blended mixture of 4.25 g. of the above prepared pyrimidine and 9.0 g. of p-chlorothiophenol is heated in an oil bath maintaining the temperature at 160°C. for 3 hours. After being cooled to room temperature, the reaction mixture is triturated with 60 ml. of 30°/o sodium hydroxide. The product is collected on a sintered glass funnel and washed with water repeatedly. Recrystallization from dimethylformamide affords 3.5 g. of 2-(3-chlorophenyl)-4-(4-chlorophenylthio)-6-(4-methylpiperazin-1-yl)-pyrimidine, hydrochloride, m.p. 254°–256°C. (dec.).

Anal. for $C_{21}H_{20}N_4SCl_3$: Calcd. C, 53.91; H, 4.53; N, 11.98; S, 6.85; Cl, 22.74. Found: C, 53.61; H, 4.55; N, 11.51; S, 6.7; Cl, 22.3.

The latter product when evaluated in the foregoing pharmacological procedure showed decreased motor activity in the host at a dosage of 40 MPK and decreased respiration of the host at a dose of 127 MPK.

EXAMPLE XXI

Repeating the procedure of Example XX 7.2 g. of 4,6-dichloro-2-(p-tolyl)-pyrimidine and 6.0 g. of N-methylpiperazine are reacted in 40 ml. of absolute ethanol. The crude product (8.4 g.) is separated and twice recrystallized from n-heptane to afford 4-chloro-6-(4-methyl-1-piperazinyl)-2-(4-tolyl)-pyrimidine, m.p. 93°–95°C.

Anal. for $C_{16}H_{19}N_4Cl$: Calcd. C, 63.46; H, 6.32; N, 18.50; Cl, 11.71. Found: C, 63.71; H, 6.59; N, 18.56; Cl, 11.5.

The above prepared compound (4.5 g.) is then reacted with 9.0 g. of p-chlorothiophenol for one hour. Recrystallization of the crude product (5.85 g.) from absolute ethanol with the addition of a few pellets of potassium hydroxide affords 4-(4-chlorophenylthio)-6-(4-methyl-1-piperazinyl)-2-(4-tolyl)-pyrimidine, m.p. 103.5°–105°C.

Anal. for $C_{22}H_{23}N_4SCl$: Calcd. C, 61.20; H, 4.92; N, 5.95; S, 6.81; Cl, 7.54. Found: C, 60.84; H, 4.74; N, 6.15; S, 6.7; Cl, 7.5.

In a similar manner, the above prepared 4-chloro-6-(4-methyl-1-piperazinyl)-2-(4-tolyl)-pyrimidine is reacted with p-ethoxythiophenol to afford 4-(4-ethoxyphenylthio)-6-(4-methyl-1-piperazinyl)-2-(4-tolyl)-pyrimidine.

EXAMPLE XXII

Employing the procedure of Example XX, 7.2 g. of 4,6-dichloro-2-(4-tolyl)-pyrimidine is reacted with N-(β-aminoethyl)-morpholine to produce 7.7 g. of 4-chloro-6-[2-(morpholino)ethylamino]-2-(4-tolyl)-pyrimidine, m.p. 123°–125°C.

Anal. for $C_{17}H_{21}N_4OCl$: Calcd. C, 61.34; H, 6.36; N, 16.84; Cl, 10.65. Found: C, 61.42; H, 6.49; N, 16.87; Cl, 10.87.

Reacting the above prepared pyrimidine (4.3 g.) with p-chlorothiophenol (9.0 g.), there is obtained 4-(4-chlorophenylthio)-6-(2-morpholinoethylamino)-2-(4-tolyl)-pyrimidine (6.9 g.), m.p. 141°–142.5°C.

Anal. for $C_{23}H_{25}N_4SOCl$: Calcd. C, 62.64; H, 5.71; N, 12.71; S, 7.27; Cl, 8.04. Found: C, 62.66; H, 5.82; N, 12.51; S, 7.5; Cl, 8.2.

EXAMPLE XXIII

Employing the procedure of Example XX, 7.7 g. of 4,6-dichloro-2-(4-methoxyphenyl)-pyrimidine is reacted with 6.0 g. of N-methylpiperazine in 45 ml. of absolute ethanol to afford 4-chloro-2-(4-methoxyphenyl)-6-(4-methyl-1-piperazinyl)-pyrimidine, m.p. 88°–90°C.

Anal. for $C_{16}H_{19}N_4OCl$: Calcd. C, 60.28; H, 6.01; N, 17.58; Cl, 11.12. Found: C, 60.19; H, 6.07; N, 17.86; Cl, 11.2.

Reacting the above prepared pyrimidine (5.8 g.) with p-chlorothiophenol (12 g.), there is obtained 4-(4-chlorophenylthio)-2-(4-methoxyphenyl)-6-(4-methylpiperazin-1-yl)pyrimidine (3.0 g.), m.p. 143°–145°C.

Anal. for $C_{22}H_{23}N_4SOCl$: Calcd. C, 61.88; H, 5.43; N, 13.12; S, 7.51. Found: C, 61.64; H, 5.33; N, 12.91; S, 7.5.

The latter product when evaluated in the foregoing pharmacological procedure showed decreased motor activity at a dosage of 12.7 MPK and decreased respiration at a dosage of 127 MPK in the host.

In the same manner, the above prepared 4-chloro-2-(4-methoxyphenyl)-6-(4-methyl-1-piperazinyl)-pyrimidine is reacted with p-propoxythiophenol to afford 2-(4-methoxyphenyl)-6-(4-methyl-1-piperazinyl)-4-(4-propoxyphenylthio)-pyrimidine.

EXAMPLE XXIV

To 50 ml. of 20% ethanolic ethyl amine there is added 10 g. of 4,6-dichloro-2-phenylpyrimidine. The reaction mixture is heated for 10 minutes on a steam-bath and evaporated to dryness in a rotary evaporator in vacuo. Upon the addition of 175 ml. of water to the residual oil, a crystalline product is deposited which amount to 10.8 g., m.p. 62°–65°C. Recrystallization from petroleum ether (b.p. 30°–60°C.)-n-pentane affords 6.7 g. of 4-chloro-6-ethylamino-2-phenyl-pyrimidine, m.p. 65.5°–67°C.

Anal. for $C_{12}H_5N_3Cl$: Calcd. C, 61.67; H, 5.18; N, 17.98; Cl, 15.17. Found: C, 61.72; H, 4.99; N, 18.4; Cl, 14.8.

A mixture of 0.7 g. of the above prepared 4-chloro-6-ethylamino-2-phenylpyrimidine and 5 g. of p-chlorothiophenol is heated to a temperature of 190°C. for three hours, then poured into 200 ml. of water after cooling. The aqueous mixture is basified with 10% sodium hydroxide solution. The oily residue which deposits crystallizes on cooling to afford 0.9 g. of material, m.p. 80°–100°C. Recrystallization from cyclohexane affords 0.4 g. of 4-(4-chlorophenylthio)-6-ethylamino-2-phenylpyrimidine, m.p. 109°–110.5°C.

Anal. for $C_{18}H_{16}N_3SCl$: Calcd. C, 63.24; H, 4.72; N, 12.29; Cl, 10.37; S, 9.38. Found: C, 63.11; H, 4.49; N, 12.28; Cl, 10.3; S, 9.5.

The latter compound when evaluated in the foregoing pharmacological procedure showed decreased respiration and decreased motor activity in the host at a dose of 40 MPK.

In a similar manner, the following compounds are prepared:

6-methylamino-2-phenyl-4-phenylthiopyrimidine;
4-(4-bromophenylthio)-2-phenyl-6-propylaminopyrimidine; and
6-butylamino-2-(4-tolyl)-4-(4-tolyl)thiopyrimidine.

EXAMPLE XXV

A well blended mixture of 2.0 g. 4-chloro-6-(4-methyl-1-piperazinyl)-2-phenylpyrimidine and 5.0 g. of p-bromothiophenol is heated in an oil bath maintaining the temperature at 160°C. for three hours. After being cooled to room temperature, the reaction mixture is triturated with 60 ml. of 30% sodium hydroxide. The product is collected on a sintered glass funnel and washed with water repeatedly. Upon recrystallization from absolute ethanol, there is obtained 4-(4-bromophenylthio)-6-(4-methyl-1-piperazinyl)-2-phenylpyrimidine.

Similarly, 4-chloro-6-(4-methyl-1-piperazinyl)-2-phenylpyrimidine is reacted with p-propylthiophenol to afford 6-(4-methyl-1-piperazinyl)-2-phenyl-4-(4-propylphenylthio)pyrimidine.

EXAMPLE XXVI

A mixture of 6-amino-4-chloro-2-phenylpyrimidine and 10 ml. of thiophenol is heated under reflux for three hours, then poured into 300 ml. of water. The reaction mixture is basified with 40% sodium hydroxide solution. The semisolid product which is deposited crystallizes on cooling to afford 6.9 g. of product. Recrystallization of this product from cyclohexane affords 4.5 g. of 4-amino-2-phenyl-6-phenylthiopyrimidine, m.p. 109°–111°C.

Anal. for $C_{16}H_{13}N_3S$: Calcd. C, 68.79; H, 4.69; N, 15.04; S, 11.48. Found: C, 69.00; H, 4.44; N, 14.77; S, 11.2.

The latter product when evaluated in the foregoing pharmacological procedure showed decreased motor activity at 127 MPK and decreased respiration at a dose of 400 MPK in the host.

Similarly, 5 g. of 4-amino-6-chloro-2-phenyl-pyrimidine is reacted with 12 ml. of m-tolylthiophenol to afford 2.6 g. of 4-amino-2-phenyl-6-(3-tolylthio)-pyrimidine, m.p. 113°–114.5°C.

Anal. for $C_{17}H_{15}N_3S$: Calcd. C, 69.59; H, 5.15; N, 14.32; S, 10.93. Found: C, 69.86; H, 4.79; N, 14.01; S, 10.7.

The latter product when evaluated in the foregoing pharmacological procedure showed decreased motor activity in the host at a dose of 127 MPK and decreased respiration at a dose of 400 MPK.

EXAMPLE XXVII

A mixture of 5 g. of 4-amino-6-chloro-2-phenyl-pyrimidine and 15 ml. of 4-chlorobenzyl mercaptan is heated under reflux for 45 minutes, then poured into 30 ml. of a 40% sodium hydroxide solution. A solid separates which after recrystallization from cyclohexane gives 2.3 g. of 4-amino-6-(4-chlorobenzylthio)-2-phenylpyrimidine, m.p. 138°–140.5°C.

Anal. for $C_{17}H_{14}N_3SCl$: Calcd. C, 62.28; H, 4.30; N, 12.82; Cl, 10.81; S, 9.78. Found: C, 62.61; H, 4.12; N, 12.81; Cl, 11.4; S, 10.0.

The latter product when evaluated in the foregoing pharmacological procedure showed decreased motor activity in the host at a dose of 127 MPK.

In the above described manner, the following compounds are obtained:

4-amino-6-benzylthio-2-phenylpyrimidine;
4-(4-chlorobenzylthio)-6-(2-methoxyethylamino)-2-(4-methoxyphenyl)-pyrimidine;

2-(4-chlorophenyl)-4-(4-fluorobenzylthio)-6-[(2-dimethylaminoethyl)amino]-pyrimidine;
4-amino-6-(4-bromobenzylthio)-2-phenylpyrimidine;
2-(4-methoxyphenyl)-4-(4-methylbenzylthio)-6-[(3-diethylamino)propylamino]-pyrimidine;
4-ethylamino-6-(4-methoxybenzylthio)-2-phenyl-pyrimidine;
4-amino-2-phenyl-6-(4-propoxybenzylthio)-pyrimidine; and
4-(4-ethoxybenzylthio)-6-[2-(morpholinoethyl)-amino]-2-phenylpyrimidine.

EXAMPLE XXVIII

6-Chloro-4-[2-(dimethylamino)ethyl]amino-2-phenylpyrimidine is obtained, as in Example VII, from 7.0 g. of 4,6-dichloro-2-phenylpyrimidine and 30 ml. of N,N-dimethylethylenediamine. The crude product thus obtained is mixed with 15.0 g. of p-chlorothiophenol, and heated in an oil bath maintaining the temperature at 160°C. for 3 hours. The reaction product is treated as in Example XXIV to give 8.3 g. of product, m.p. 140°-145°C. Recrystallization from 95% ethanol affords 4-(4-chlorophenylthio)-6-[(2-dimethylamino)ethylamino]2-phenyl-pyrimidine, m.p. 147°-149°C.

Anal. for $C_{20}H_{21}N_4SCl$: Calcd. C, 62.40; H, 5.50; N, 14.89; S, 8.33. Found: C, 62.46; H, 5.21; N, 14.91; S, 8.5.

Employing the above procedure, 7.0 g. of 4,6-dichloro-2-phenylpyrimidine is reacted with 34 ml. of N,N-diethylethylenediamine, followed by the reaction of the crude product thereof with 12.5 g. of p-chlorothiophenol. Recrystallization of the crude product (3.85 g.) from n-heptane affords 4-(4-chlorophenylthio)-6-[2-(diethylamino)ethylamino]-2-phenylpyrimidine, m.p. 83.5°-86°C.

Anal. for $C_{22}H_{25}N_4SCl$: Calcd. C, 63.98; H, 6.10; N, 13.57; S, 7.76. Found: C, 63.78; H, 5.88; N, 13.65; S, 7.4.

EXAMPLE XXIX

A mixture of 5.2 g. of 4,6-dichloro-2-(m-chlorophenyl)-pyrimidine, 2.7 g. of aminoacetaldehyde diethyl acetal and 20 ml. of ethanol is heated under reflux for 1 hour and then concentrated in vacuo on a rotary evaporator. The residual solid is recrystallized from methanol affording 4.5 g. of 4-chloro-2-(3-chlorophenyl)-6-[(2-diethoxyethyl)amino]pyrimidine, m.p. 99°-101°C.

Anal. for $C_{20}H_{19}N_4SOCl$: Calcd. C, 53.94; H, 5.38; N, 11.80; Cl, 19.90. Found: C, 54.08; H, 5.43; N, 12.11; Cl, 19.40.

The above prepared compound is then reacted with p-chlorothiophenol, as in Example XXIV, to produce 2-(3-chlorophenyl)-4-(4-chlorophenylthio)-6-[(2-diethoxyethyl)amino]-pyrimidine.

In a similar manner, 2-(4-chlorophenyl)-4-(4-methoxyphenylthio)-6-[(2-dimethoxyethyl)amino]-pyrimidine is synthesized.

EXAMPLE XXX

A mixture of 5.14 g. of 4-amino-6-chloro-2-phenylpyrimidine and 10.1 g. of p-chlorothiophenol is heated in an oil bath maintaining a temperature of 150°C. for twenty minutes. The reaction mixture is triturated with hot 10% sodium hydroxide. The product is collected on a filter, and washed with water repeatedly. The crude product weighs 8.0 g. and melts at 118°-121°C.

Upon recrystallization from cyclohexane, there is obtained 4-amino-6-(4-chlorophenylthio)-2-phenylpyrimidine, m.p. 124°-125°C.

Anal. for $C_{16}H_{12}N_3SCl$: Calcd. C, 61.24; H, 3.86; N, 13.39; S, 10.22; Cl, 11.30. Found: C, 60.96; H, 3.97; N, 13.66; S, 10.4; Cl, 11.2.

The latter product when evaluated in the foregoing pharmacological procedure showed decreased motor activity in the host at a dosage of 127 MPK.

What is claimed is:

1. A compound selected from the group consisting of those having the formula:

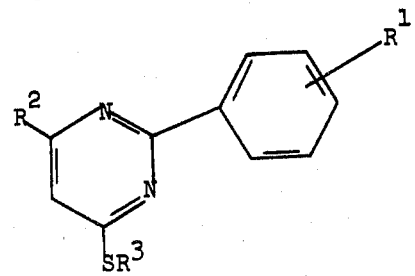

wherein $R^1$ is selected from the group consisting of hydrogen, dichloro, halogen, methyl, ethyl, propyl and methoxy; $R^2$ is selected from the group consisting of amino, 4-methylpiperazino, 4-ethylpiperazino, methoxyethylamino, methoxypropylamino, 4-hydroxyethylpiperazino, hydroxyethylamino, hydroxypropylamino, hexahydroazepinyl, dimethoxyethylamino; diethyoxyethylamino, methylamino, ethylamino, propylamino and butylamino; and $R^3$ is selected from the group consisting of phenyl, halophenyl, ethylphenyl, methoxyphenyl, ethoxyphenyl, propoxyphenyl, benzyl, halobenzyl, methylbenzyl, methoxybenzyl, ethoxybenzyl and propoxybenzyl.

2. A compound as described in claim 1 which is: 4-amino-2-phenyl-6-phenylthiopyrimidine.

3. A compound as described in claim 1 which is 4-(4-methyl-1-piperazinyl)-2-phenyl-6-phenylthiopyrimidine.

4. A compound as described in claim 1 which is: 4-amino-2-phenyl-6-(3-tolylthio)-pyrimidine.

5. A compound as described in claim 1 which is: 4-amino-6-(4-chlorophenylthio)-2-phenylpyrimidine.

6. A compound as described in claim 1 which is: 4-(4-chlorophenylthio)-6-ethylamino-2-phenylpyrimidine.

7. A compound as described in claim 1 which is: 4-(4-chlorophenylthio)-6-(4-methyl-1-piperazinyl)-2-phenylpyrimidine.

8. A compound as described in claim 1 which is: 4-(4-chlorophenylthio-6-[2-(methoxyethyl)amino]-2-phenylpyrimidine.

9. A compound as described in claim 1 which is: 4-[4-(4-chlorophenylthio)-2-phenyl-6-pyrimidinyl]-1-piperazine ethanol.

10. A compound as described in claim 1 which is: N-[2-(6-[4-chlorophenylthio]-2-phenylpyrimidin-4-ylamino)ethyl]-acetamide.

11. A compound as described in claim 1 which is: 2-(4-chlorophenyl)-4-(4-chlorophenylthio)-6-(4-methyl-piperazin-1-yl)-pyrimidine.

12. A compound as described in claim 1 which is: 2-(4-chlorophenyl)-4-(4-chlorophenylthio)-6- [(2-methoxyethyl)-amino]-pyrimidine.

13. A compound as described in claim 1 which is: 2-(3-chlorophenyl)-4-(4-chlorophenylthio)-6-(4-methylpiperazin-1-yl)-pyrimidine, hydrochloride.

14. A compound as described in claim 1 which is: 4-(4-chlorophenylthio)-6-(4-methyl-1-piperazinyl)-2-(4-tolyl)-pyrimidine.

15. A compound as described in claim 1 which is: 4-(4-chlorophenylthio)-6-(2-methoxyethylamino)-2-(4-tolyl)pyrimidine.

16. A compound as described in claim 1 which is: 4-[4-(4-chlorophenylthio)-2-(4-tolyl)pyrimidin-6-yl]-1-piperazine ethanol.

17. A compound as described in claim 1 which is: 4-(4-chlorophenylthio)-2-(4-methoxyphenyl)-6-(4-methylpiperazin-1-yl)-pyrimidine.

18. A compound as described in claim 1 which is: 6-(4-chlorophenylthio)-4-(2-methoxyethylamino)-2-(4-methoxyphenyl)-pyrimidine.

19. A compound as described in claim 1 which is: 4-amino-6-(4-chlorobenzylthio)-2-phenylpyrimidine.

20. A compound as described in claim 1 which is: 4-(4-chlorophenylthio)-2-(3,4-dichlorophenyl)-6-[2-(dimethylamino)ethylamino]-pyrimidine[.½ cyclohexane].

* * * * *